(12) United States Patent
Baaijens et al.

(10) Patent No.: US 10,898,673 B2
(45) Date of Patent: *Jan. 26, 2021

(54) COLOR LIGHTING SYSTEM TO INFLUENCE PERCEPTION OF AMBIENT TEMPERATURE

(71) Applicant: SIGNIFY HOLDING B.V., Eindhoven (NL)

(72) Inventors: Johannes Petrus Wilhelmus Baaijens, Eindhoven (NL); Simone Helena Maria Poort, Veldhoven (NL); Lucas Josef Maria Schlangen, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 30 days.

This patent is subject to a terminal disclaimer.

(21) Appl. No.: 16/354,361

(22) Filed: Mar. 15, 2019

(65) Prior Publication Data
US 2019/0209807 A1    Jul. 11, 2019

Related U.S. Application Data

(60) Division of application No. 14/299,036, filed on Jun. 9, 2014, now Pat. No. 10,252,022, which is a (Continued)

(30) Foreign Application Priority Data

Jun. 24, 2009   (EP) .................................... 09163647

(51) Int. Cl.
*A61M 21/02* (2006.01)
*F24F 3/056* (2006.01)
(Continued)

(52) U.S. Cl.
CPC ............ *A61M 21/02* (2013.01); *A61M 21/00* (2013.01); *F24F 3/056* (2013.01); *F24F 11/30* (2018.01);
(Continued)

(58) Field of Classification Search
CPC .................. A61M 21/02; A61M 21/00; A61M 2021/0044; A61M 2021/0066;
(Continued)

(56) References Cited

U.S. PATENT DOCUMENTS

| 5,645,578 A | 7/1997 | Daffer et al. |
| 8,795,344 B2 | 8/2014 | Baaijens et al. |

(Continued)

FOREIGN PATENT DOCUMENTS

| JP | 2001275872 A | 10/2001 |
| JP | 2003288995 A | 10/2003 |

(Continued)

OTHER PUBLICATIONS

Webb, "Considerations for Lighting in the Built Environment: Non-Visual Effects of Light" 2006 pp. 721-727.

(Continued)

*Primary Examiner* — Aaron F Roane
(74) *Attorney, Agent, or Firm* — Meenakshy Chakravorty

(57) ABSTRACT

A lighting control device for influencing thermoregulation of a vertebrate is disclosed. In one example, the lighting control device configured to select, on the basis of a predetermined criterion, a particular group of colors of groups having been categorized into groups on the basis of dominant wavelength, where each group of colors is arranged to influence a vertebrate's thermoregulation in a particular manner, and configured to generate a control signal for controlling the dominant wavelength of light emitted from at least one light source in accordance with the selected group of colors. The (Continued)

lighting control device is configured to transmit the generated control signal to said at least one light source for said at least one light source to emit light of the selected group of colors, thereby influencing the thermoregulation of the vertebrate being exposed to the light on the basis of said predetermined criterion.

14 Claims, 4 Drawing Sheets

Related U.S. Application Data continuation of application No. 13/380,527, filed as application No. PCT/IB2010/052674 on Jun. 15, 2010, now Pat. No. 8,795,344.

(51) Int. Cl.
| | |
|---|---|
| F24F 11/30 | (2018.01) |
| H05B 45/20 | (2020.01) |
| H05B 47/155 | (2020.01) |
| A61M 21/00 | (2006.01) |
| G05B 15/02 | (2006.01) |
| F24F 110/10 | (2018.01) |

(52) U.S. Cl.
CPC ........... *H05B 45/20* (2020.01); *H05B 47/155* (2020.01); *A61M 2021/0044* (2013.01); *A61M 2021/0066* (2013.01); *F24F 2110/10* (2018.01); *G05B 15/02* (2013.01); *G05B 2219/163* (2013.01); *G05B 2219/25011* (2013.01); *G05B 2219/2642* (2013.01); *H01H 2300/03* (2013.01); *Y02B 20/40* (2013.01)

(58) Field of Classification Search
CPC ........ F24F 11/30; F24F 3/056; F24F 2110/10; H05B 45/20; H05B 47/155; H05B 2300/03; G05B 15/02; G05B 2219/163; G05B 2219/25011; G05B 2219/2642; Y02B 20/40
USPC ........................................................... 600/27
See application file for complete search history.

(56) References Cited

U.S. PATENT DOCUMENTS

| | | | |
|---|---|---|---|
| 2003/0231495 | A1 | 12/2003 | Searfoss |
| 2004/0260364 | A1* | 12/2004 | Daffer .................... A61H 33/06 607/81 |
| 2008/0123332 | A1* | 5/2008 | Searfoss .................. A61B 5/00 362/231 |
| 2008/0231214 | A1 | 9/2008 | Kim et al. |

FOREIGN PATENT DOCUMENTS

| | | |
|---|---|---|
| JP | 2004254141 A | 9/2004 |
| JP | 2005128976 A | 5/2005 |
| JP | 2006076959 A | 3/2006 |
| JP | 2009521806 A | 6/2009 |

OTHER PUBLICATIONS

Nakamura et al., "Influence of Air Temperature on Preference for Color Temperature of General Lighting in the Room," 2000, pp. 41-47, vol. 4, No. 1.

* cited by examiner

COLOR LIGHTING SYSTEM TO INFLUENCE PERCEPTION OF AMBIENT TEMPERATURE

FIELD OF THE INVENTION

The present invention relates to a method of influencing thermoregulation of a vertebrate and a lighting control device for doing the same. The present invention further relates to a climate control system.

BACKGROUND OF THE INVENTION

Lighting is known to be an important factor for controlling indoor environment. Light facilitates perception, can create a pleasant atmosphere and provides a powerful stimulus to our biological clock, thus supporting a healthy activity—sleep cycle.

The human circadian (24 hr) rhythm is accompanied by a 24-hour, almost sine wave-shaped, variation of the core body temperature (CBT) of the human body. The peak-to-peak value of the CBT variation is typically some 0.7 degrees centigrade. The CBT minimum usually occurs at night, around 1-2 hours before spontaneous wake-up. Nocturnal darkness is associated with a peak in secretion of the hormone melatonin. Melatonin reinforces darkness-related behavior, which for humans implies sleep. Sleep is associated with lower temperatures while activity is associated with higher temperatures. A temperature difference between distal skin (hands, feet) and proximal skin (thigh, stomach) may promote onset of sleep. For rapid sleep onset it is essential that the body can discharge heat by using distal skin regions to dissipate heat from the core body to the environment, allowing the core body temperature to drop. This demonstrates that thermoregulation can be used as a means to control sleepiness of an individual. Exposure to nocturnal light suppresses nocturnal melatonin secretion, thus influencing thermoregulation as the melatonin peak is usually associated with the minimum in CBT. By influencing the melatonin levels and phase shifting the biorhythm, light has an indirect influence on thermoregulation.

It is less well known that light also has a direct influence on thermoregulation in humans. Bright light exposure decreases the core body temperature, even during exercise. The higher the color temperature of the light source, the stronger this effect, although at high levels saturation of this effect may occur. The CBT lowering effect of bright light exposure may persist several hours after exposure has ended. Bright light exposure over several hours during the daytime appears to lower the CBT threshold above which cutaneous vasodilatation and forearm sweating occurs.

After daytime bright light exposure, subjects felt less cold during chilly afternoons or evenings. These findings indicate a reduced set point of core body temperature caused by the influence of bright light exposure in the daytime. The reduced CBT set point also has an effect on skin blood flow. In cold environments, the dermal blood flow has to increase to promote heat loss so that the CBT can be kept at a lower level.

Not only the light intensity is known to be thermoregulating, also the color temperature of the light can be used for thermoregulation. When comparing 3000, 5000 and 7500 K lighting, the increase in rectal temperature just after hot bathing (40° C.) is greatest under bathroom lighting of 3000K and the higher value was maintained after bathing. This conforms to the observation that light of a higher color temperature results in a lower set point of the CBT. When an individual is bathing, the dermal blood flow has to be low, so that the CBT increase due to heat absorption from the bath is minimal. When the CBT set point decreases, the dermal blood flow further decreases in an attempt to minimize heating of the body core. However, upon leaving the hot water, the individual's dermal blood flow quickly rises. This enables an individual to get rid of the excess heat, thus allowing the CBT to decrease to its set point. A lower CBT set point will increase the dermal blood flow after the bath and will reduce the individual's drop in skin temperature after exiting the water.

To conclude, it can be said that the intensity and the color temperature of the lighting have a direct influence on thermoregulation of a vertebrate being exposed to the lighting. Scientific results indicate that the set point of the core body temperature decreases with increasing intensity and color temperature.

International patent application having publication number WO 2008/120127 generally discloses an interaction system and user interface for mimicking and controlling natural daylight such as by changing attributes of artificial light throughout the day or other time periods, for example, in response to manipulating an input device, such as a knob, a slider, a pointer and/or selectable dials having indicators. In more detail, WO 2008/120127, which is assigned to the present assignee, discloses an interactive lighting control system that includes a user interface operationally coupled to a processor. The processor is also coupled to a memory and is configured to receive user inputs from a user interface and to control at least one light source in accordance with the user input (received from the user interface) and/or upon execution of predetermined programs or light scripts stored in the memory. The light scripts include instructions to control the light sources to provide predetermined static and/or dynamically changing illumination as a function of one or various factors, such as time of day, day of year, season, weather, etc., by changing light attributes provided from the various light sources, such as intensity (i.e., dimming function), color, hue, saturation, direction and the like. Thus, the system of WO 2008/120127 facilitates natural daylight mimicking, and does not tackle the above discussed issues related to thermoregulation.

SUMMARY OF THE INVENTION

It is an object of the present invention to provide a method of and a lighting control device for influencing thermoregulation of a vertebrate.

This object is achieved by the present invention as defined by the independent claims. Preferred embodiments are defined by the dependent claims.

According to a first aspect of the invention, there is provided a method of influencing thermoregulation of a vertebrate, which method comprises the step of selecting, on the basis of a predetermined criterion, a particular group among a plurality of groups of color of light. The color of light has been categorized into groups on the basis of dominant wavelength of specific colors, where each group of colors is arranged to influence the thermoregulation of a vertebrate in a particular manner. Further, the method comprises the steps of generating a control signal for controlling the dominant wavelength of light emitted from at least one light source in accordance with the selected group of colors, and transmitting the generated control signal to the light source(s) for the light source(s) to emit light of the selected group of colors, thereby influencing the thermoregulation of a vertebrate being exposed to the light of the selected group of colors emitted by the light source(s) on the basis of the predetermined criterion.

According to a second aspect of the invention, there is provided a lighting control device for influencing thermoregulation of a vertebrate, said device comprising a processor and a transmitter. The processor is arranged to select, on the basis of a predetermined criterion, a particular group among a plurality of groups of color of light. The color of light has been categorized into groups on the basis of the dominant wavelength of the respective color, wherein each group of colors is arranged to influence the thermoregulation of a vertebrate in a particular manner. The processor is further arranged to generate a control signal for controlling the dominant wavelength of light emitted from at least one light source in accordance with the selected group of colors. The transmitter is arranged to transmit the generated control signal to the light source(s) for the light source(s) to emit light of the selected group of colors, thereby influencing the thermoregulation of a vertebrate being exposed to the light of the selected group of colors emitted by the light source(s) on the basis of the predetermined criterion.

According to a third aspect of the invention, there is provided a climate control system arranged to be connectable to the inventive lighting control device. The system comprises a climate control device being arranged to be responsive to the control signal generated by the processor of the lighting control device, wherein characteristics of fluid discharged by the climate control device are adapted in accordance with the predetermined criterion.

A basic idea of the invention is to categorize color of light into groups on the basis of color dominant wavelength. Colors giving a feeling of elevated ambient temperatures are colors between red and yellow (e.g. red, orange, yellow-orange, pure yellow) on the so called hue circle; i.e. in terms of dominant wavelength $\lambda_d$, colors with 576 nm$<\lambda_d<$700 nm. Colors giving a feeling of lower ambient temperatures are colors between green and blue on the hue circle (e.g. green, cyan, blue); i.e. in terms of dominant wavelength $\lambda_d$, colors with 460 nm$<\lambda_d<$520 nm. Thus, each group of colors is arranged to affect an individual's perception of ambient temperature in a particular manner, or to actually affect the individual's physiological thermoregulation. That is, not only the perception of ambient temperature may be affected, but also the internal physiological process of the individual, since the individual's core body temperature may be affected. The hue of a color can be viewed upon as a perceptual attribute, while the dominant wavelength is its physical analog.

After having categorized the colors into different groups, a particular group of colors may be selected on the basis of a predetermined criterion, one criterion being that an individual is to perceive the ambient temperature as higher than it actually is, while another criterion may be that the individual is to perceive the ambient temperature as lower than it actually is. Thereafter, a control signal is generated for controlling the dominant wavelength of light emitted from at least one light source in accordance with the selected group of colors. Finally, the generated control signal is transmitted to the light source(s) to be controlled, thereby influencing the thermoregulation of an individual being exposed to the light source(s) on the basis of the predetermined criterion.

The present invention is advantageous, in that colored lighting is employed for changing an individual's perception of ambient temperature, which enables energy savings for heating and air conditioning systems. Using a lighting control device for varying the color of light results in a flexible solution, since the device easily facilitates changing to an environment that is perceived as warmer or as cooler than the actual room temperature. Obviously, this cannot be achieved as easily with conventional solutions like painting walls. The present invention may advantageously be used for illuminating walls and/or ceilings, pillars, etc., or creating luminous walls, ceilings, floors, etc. The intensity and/or the color of the light can be adjusted, for instance depending on the time of day or a subjective experience, such as an individual feeling hot or cold.

Further, in accordance with an embodiment of the invention, to better attain an increased or decreased perceived ambient temperature, the colors need to have a sufficient level of saturation. These levels are typically defined by the CIE1931 chromaticity diagram, which is known to a skilled person. Moreover, the level of saturation for a certain hue is also determined by the choice of the reference white point. Choosing the white point in the color system at 6500 K (daylight) would be a universal choice, suitable for both warm and cool colors. This could also be used for the ambient white lighting present in an indoor space. Thus, when categorizing color of light into groups, color saturation is also advantageously taken into account, and properties defined by the CIE1931 chromaticity diagram may form a basis for the categorizing of color of light into groups. However, the experience of "warm" or "cool" hues can be enhanced by also adjusting the color temperature of the ambient white light.

In an alternative embodiment, the perceived "warmth" of colors or hues can be enhanced by adjusting the color temperature of the reference white point. By using a white point color temperature below 3000 K, warmth may be enhanced in that a "warm" white point is combined with warm hues.

In another embodiment of the present invention, the lighting control device is arranged to be connectable to a thermometer providing the lighting control device with a measure of the ambient temperature, which ambient temperature thus forms the predetermined criterion for controlling light. In an example, on a summer day, the room temperature is measured to be 25° C. and fed back to the device. As an alternative (or complement to) lowering the temperature, a "cool" color of light, e.g. blue, may be selected. An individual being exposed to the light source will hence perceive the ambient temperature as being lowered.

Further, a great advantage of the present invention is that energy consumption of climate and/or heating control systems such as air-conditioners can be decreased, since a human being perceives the ambient temperature as higher or lower when he is exposed to light of a certain color. Thus, by exposing an individual to light of a "warm" color, e.g. red or yellow, it is possible to lower the ambient temperature and still have the individual perceive the ambient temperature as being the same as it was before actually lowering it. By exposing an individual to light of a "cool" color, the individual will perceive the ambient temperature as cooler, thereby lowering the need for air-conditioning systems. Hence, great energy savings are possible for heating and climate systems.

Further provided is a climate control system being connectable to the previously described inventive lighting control device and further comprising a climate control device for intelligent climate control. Thus, the lighting control device of the present invention is combined with a HVAC (heating, ventilating and air conditioning) device, also referred to as a climate control device. In the inventive climate control system, the output of the HVAC device is responsive to the predetermined criterion for controlling the light source(s). For instance, assuming that the color of the light source(s) of the lighting system is adjusted towards the red-yellow area of the color scale, the output temperature of the climate control system may be lowered, since a "warmer" color of light will result in a higher perceived ambient temperature for the individual. Parameters of the climate control system other than temperature, such as e.g. humidity, air flow, purity, etc. may alternatively be adjusted in response to the controlled property of light. Thus, the climate control device is arranged to be responsive to the control signal generated by the processor of the lighting control device, wherein characteristics of fluid discharged by the climate control device are adapted in accordance with the predetermined criterion for controlling light.

Most of the commercially available HVAC systems are optimal in terms of energy saving and perform fairly well. However, their major drawback is that they are designed to operate in response to pure physical parameters such as temperature and/or humidity. Their weakness is that they do not employ human perception of light in order to become even more efficient in terms of energy saving. With this particular climate control system, human perception of light is taken into account to control the HVAC device output, which in turn allows greater energy efficiency.

The light sources used can be any one of LED, incandescent, halogen, fluorescent or metal-halide, etc. An individual whose thermoregulation is to be influenced can be exposed to more than one light source.

The application areas of the present invention are numerous. For example:

in offices or meeting rooms to cut energy costs on air conditioning or heating by using cool and warm colors respectively on walls or ceilings or on free-standing or pendent decorative luminaries;

in supermarkets where fresh or cooled products are present. During winter time, lower ambient temperatures may be used, while using warm colors to keep the customers comfortable. This is advantageous in that products can be kept fresh longer, particularly fruit and vegetables that are not cooled. Further, this leads to a reduction of energy consumption intended for heating supermarket premises. Additionally, energy consumption related to cooling in refrigerators and freezers can be reduced since the ambient temperature is lowered;

in supermarkets where other products are present. During summer time, higher ambient temperature may be used, while using cool colors to keep the customers comfortable. This is advantageous in that energy consumption related to usage of air conditioning for cooling the premises can be reduced;

in hotel rooms, homes, homes for elderly, hospital rooms, schools, etc., in accordance with the energy saving principles given in the above.

It is noted that the invention relates to all possible combinations of features recited in the claims. Further features and advantages of the present invention will become apparent when studying the appended claims and the following description. Those skilled in the art realize that different features of the present invention can be combined to create embodiments other than those described in the following.

BRIEF DESCRIPTION OF THE DRAWINGS

These and other aspects of the present invention will now be described in more detail, with reference to the appended drawings showing one or more embodiments of the invention.

DETAILED DESCRIPTION

Figure 1:
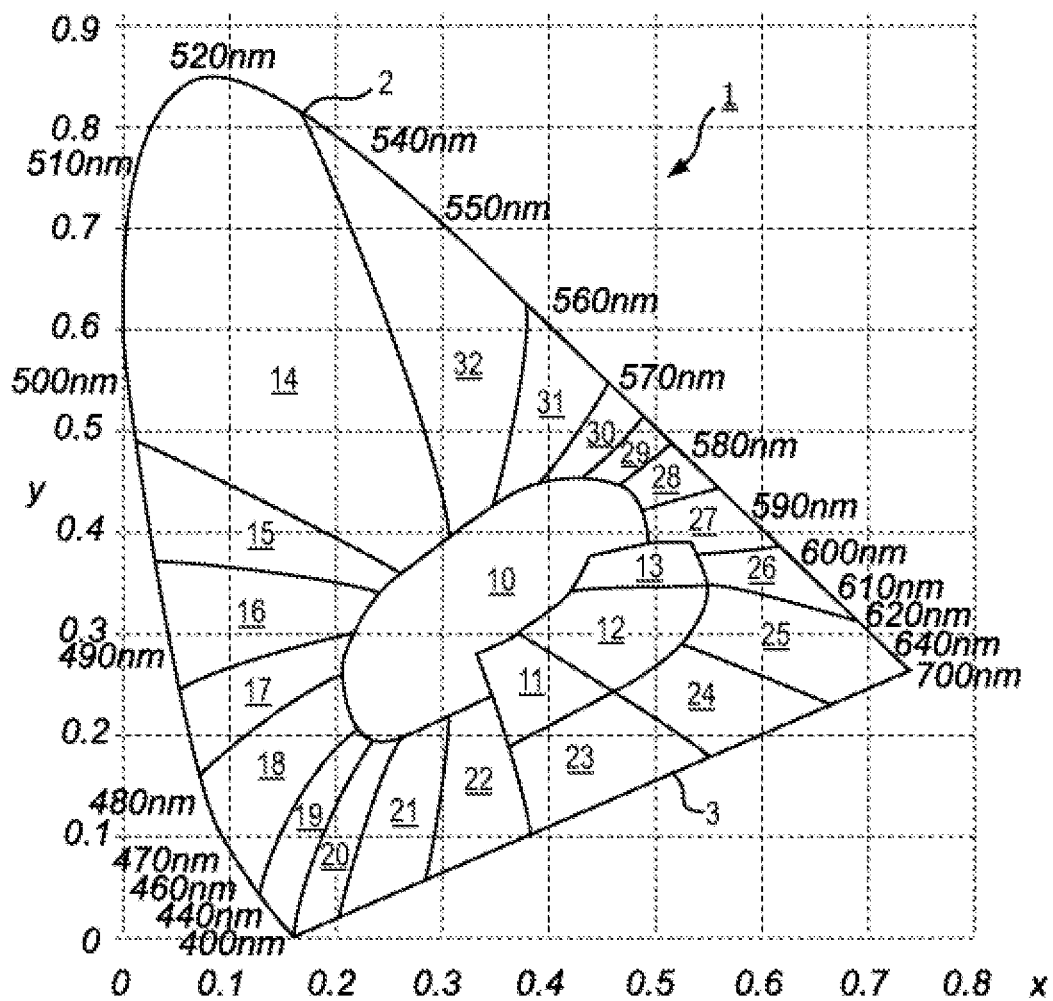
FIG. 1 shows the known CIE1931 chromaticity diagram.

FIG. 1 shows the well-known CIE1931 chromaticity diagram. The diagram represents all of the chromaticities visible to an individual. The chromaticities are approximately indicated by way of marked regions shown in the tongue-shaped area 1. The curved edge 2 of the tongue-shaped area 1 corresponds to monochromatic light of wavelengths denoted in nanometers. The straight edge 3 at the lower part of the tongue-shape area 1 has no counterpart in monochromatic light. Less saturated colors appear in the interior of the FIG. 1, with region 10 representing white at the center. Other regions shown in FIG. 1 include region 12 for pink, region 14 for green, region 18 for blue, region 25 for red and region 29 for yellow, as well as a number of further regions for colors in between. In an embodiment of the present invention, color of light is categorized into groups using properties of the CIE1931 chromaticity diagram. Colors giving a feeling of elevated ambient temperatures are colors between red, i.e. region 25, and yellow, i.e. region 29 (e.g. red, orange, yellow-orange, pure yellow) on the so called hue circle; i.e. in terms of dominant wavelength $\lambda_d$, colors with 576 nm$<\lambda_d<$700 nm. Colors giving a feeling of lower ambient temperatures are colors between green, i.e. region 14, and blue, i.e. region 18, on the hue circle (e.g. green, cyan, blue); i.e. in terms of dominant wavelength $\lambda_d$, colors with 460 nm$<\lambda_d<$520 nm.

Further, in accordance with an embodiment of the invention, to better attain an increased or decreased perceived ambient temperature, the colors need to have a sufficient level of saturation. These levels are typically defined by the CIE1931 chromaticity diagram shown in FIG. 1. Moreover, the level of saturation for a certain hue is also determined by the choice of the reference white point. Choosing the white point in the color system at 6500 K (daylight) would be a universal choice, suitable for both warm and cool colors. This could also be used for the ambient white lighting present in an indoor space. Thus, when categorizing color of light into groups, color saturation is also advantageously taken into account. However, the experience of "warm" or "cool" hues can be enhanced by also adjusting the color temperature of the ambient white light. Therefore, the diagram of FIG. 1 is used to define the range of saturation level per color region, for which the colors can be categorized as "red", "orange", "blue", etc. Moreover, it should be noted that the level of saturation for a certain hue further is determined by the choice of the reference white point:

to guarantee "warm" colors along a line through this white point and the saturated hue on the boundary of the CIE1931 chromaticity space, the color temperature of the reference white point should preferably be 6500 K (daylight) or lower, and to guarantee "cool" colors along a line through this white point and the saturated hue on the boundary of the CIE1931 chromaticity space, the color temperature of the reference white point should preferably be 6500 K (daylight) or higher.

Choosing the white point in the color diagram at 6500 K (daylight) would be a universal choice, suitable for both warm and cool colors. This white point could also be used for the ambient white lighting present in an indoor space in which the inventive lighting control device is applied.

Figure 2:
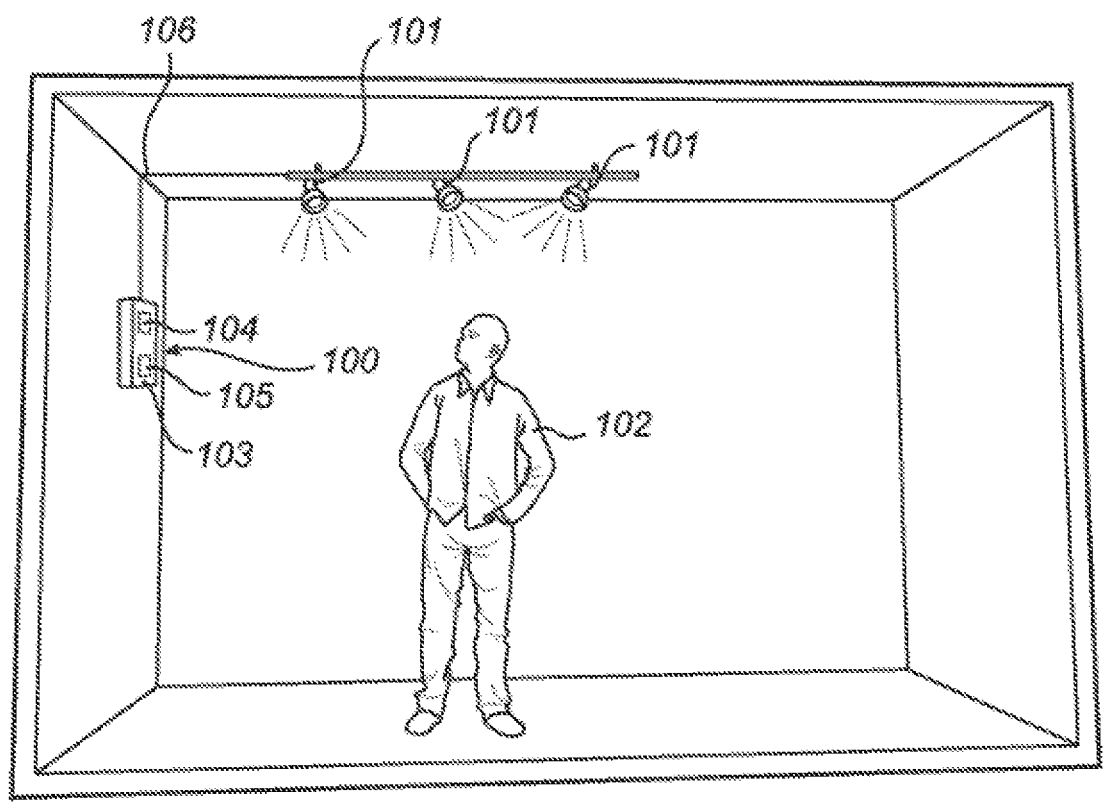
FIG. 2 shows a lighting control device according to an embodiment of the invention.

FIG. 2 shows an embodiment of a lighting control device 100 according to the present invention. An individual 102 is exposed to light from a number of light sources 101 emitting light having a certain characteristic. Conditional on the effect to be achieved, a particular group of the plurality of color of light groups is selected. The categorized groups may be stored in a memory 103 incorporated in the control device 100. Alternatively, the groups are remotely stored and the device acquires a selected group via the Internet or a wireless connection. Assuming that a predetermined criterion is that the individual should perceive the ambient temperature as cool, a group can be selected comprising a bluish color having a wavelength of about 470 nm. Thereafter, a control signal is generated by processor 104 for controlling the wavelength of light emitted from the light sources 101 in accordance with the selected (bluish) group. The control signal is transmitted by transmitter 105 incorporated in the lighting control device via leads 106 to cause the light sources to emit light of a color complying with the wavelength selected, thus influencing the thermoregulation of the exposed individual 102 in the desired direction.

In a particular embodiment, the individual may himself provide the lighting control device 100 with a subjective criterion reflecting a sensation such as "I feel cold", for example via a keypad (not shown) connected to the device.

Figure 3:
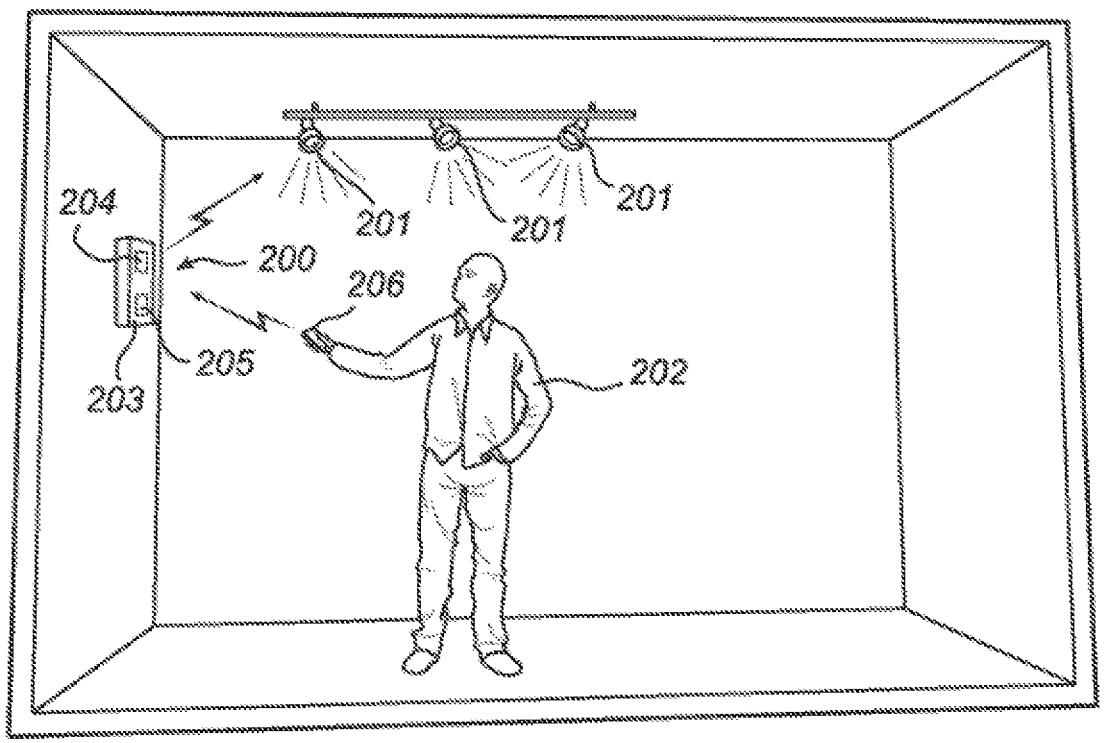
FIG. 3 shows a lighting control device according to a further embodiment of the present invention.

FIG. 3 shows a lighting control device 200 according to an embodiment of the present invention. A thermometer 206 is in communication with the lighting control device 200, for providing the device with measured values of ambient temperature. The thermometer could be a conventional thermometer mounted on a wall of the room exposed to the light sources 201, or could alternatively be embodied in the form of a sensor attached to the individual 202, for measuring ambient temperature and for wirelessly transmitting the measured value to the lighting control device. Again, in accordance with a predetermined criterion, a group of colors is selected from a plurality of groups. For instance, for an ambient temperature of 17-19° C., the criterion may be that the individual should perceive the temperature as substantially warmer, requiring the selection of a color (red) having a dominant wavelength of e.g. 670 nm, whereas for an ambient temperature of 19-21° C., the criterion may be that the individual should perceive the temperature as slightly cooler, requiring the selection of a color (orange) having a dominant wavelength of e.g. 590 nm. For an ambient temperature of 21-23° C., the criterion may be that the individual should perceive the temperature as neutral, requiring the selection of a color (yellowish green) having a dominant wavelength of e.g. 550 nm (or possibly turning the light off). On the other hand, for an ambient temperature of 23-25° C., the criterion may be that the individual should perceive the temperature as slightly cooler, requiring the selection of a color (green) having a wavelength of e.g. 510 nm, whereas for an ambient temperature of 25-27° C., the criterion may be that the individual should perceive the temperature as substantially cooler, requiring the selection of a color (blue) having a wavelength of e.g. 460 nm.

Thus, the processor 204 selects the color group in view of the criterion to be achieved, and generates a control for controlling the wavelength of light emitted from the light sources 201 in accordance with the selected color group. The control signal is wirelessly transmitted by transmitter 205 incorporated in the lighting control device to cause the light sources to emit light of a color complying with the wavelength selected, thus influencing the thermoregulation of the exposed individual 202 in an adequate manner. The sensor 206 of FIG. 3 may e.g. be implemented as a wristlet, possibly combined with an exercise device such as a pulse clock. Instead of using a transmitter, the lighting control device 200 may comprise a transceiver which is capable of receiving appropriate signals from the temperature sensor 206, as well as transmitting control signals to the light sources 201.

Figure 4:
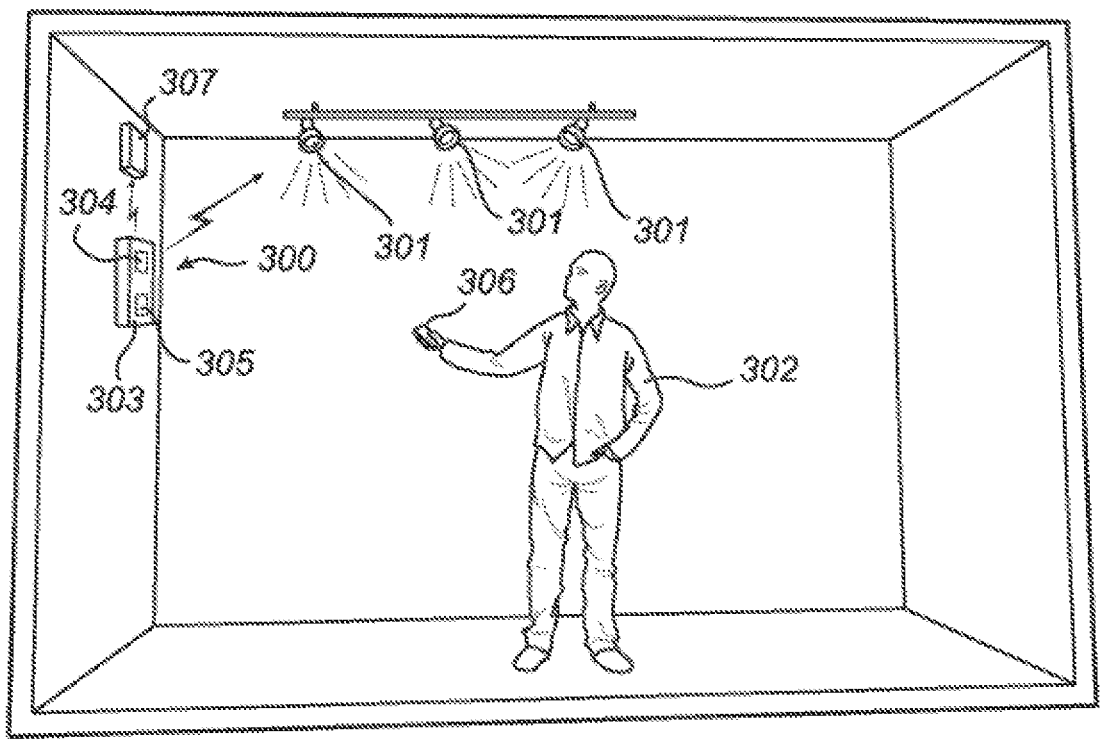
FIG. 4 shows a climate control system according to an embodiment of the present invention, which climate control system uses the lighting control device illustrated in FIGS. 2 and 3.

FIG. 4 shows a climate control system according to an embodiment of the present invention, which climate control system is connectable to the lighting control device illustrated in FIGS. 2 and 3. In the climate control system illustrated in FIG. 4, the lighting control device illustrated in FIGS. 2 and 3 is combined with a climate control device. The lighting control device 300 communicates with a number of light sources 301 emitting light having a certain characteristic, to which the individual 302 is exposed. Depending on the effect to be achieved, a particular group of the plurality of groups of color of light is selected from memory 303. Assuming that a predetermined criterion is that the individual should perceive the ambient temperature as warm, a group can be selected comprising a yellow color having a wavelength of about 575 nm. Thereafter, a control signal is generated by processor 304 for controlling the wavelength of light emitted from the light sources 301 in accordance with the selected (yellow) group. The control signal is wirelessly transmitted by transmitter 305 to cause the light sources to emit light of a color complying with the wavelength selected, thus influencing the thermoregulation of the exposed individual 302 in the desired direction. In this particular example, the light sources 301 will emit a yellow light, thereby making the individual 302 perceive the ambient temperature as warmer.

In connection to this, the transmitter 305 wirelessly communicates the control signal to the climate control device 307 to lower the heat of discharged air. In the case where the climate control device 307 is comprised in the lighting control device 300, the control signal is in general not communicated via a wireless interface, as the climate control device 307 in that case typically is comprised in the same housing as the lighting control device 300. Thus, when selecting a "warm" color to which the individual is exposed, the individual perceives the ambient temperature as being constant even though the temperature of the heat dissipated by the climate control device is reduced. Consequently, energy savings can be made.

The climate control device may comprise a user interface via which a user can program desired climate parameters, e.g. a desired set temperature of 20° C. Further, the climate control device may comprise a control algorithm which would control deviations from the temperature set by the user by automatically lowering the set temperature of discharged air when warming up, or raising the set temperature of discharged air when cooling with air con, while compensating for the deviations by having the controller adjust the color of light emitted by the light sources.

The illustrated lighting control device and climate control system typically comprise one or more microprocessors or some other device with computing capabilities, e.g. an application specific integrated circuit (ASIC), a field programmable gate array (FPGA), a complex programmable logic device (CPLD), etc., in order to control light source properties and climate control device output, while executing appropriate downloadable software stored in a suitable storage area, such as a RAM, a Flash memory or a hard disk. For intercommunication to be possible, wireless communication interfaces are provided.

The person skilled in the art realizes that the present invention by no means is limited to the preferred embodiments described above. On the contrary, many modifications and variations are possible within the scope of the appended claims. For example, the lighting control device can be implemented in many different ways, e.g. as a stand-alone lighting device, in a personal cap, in a car visor, in a pair of glasses, in the frame of a PC monitor, or in a general lighting system, etc. Another implementation may be based on the combination of the lighting control device with a backlight being part of a liquid-crystal display.

The invention claimed is:

1. A lighting control device for influencing thermoregulation of a vertebrate, said device comprising:
    a processor configured to select, on the basis of a predetermined criterion, a particular group among a plurality of groups of color of light, said color of light having been categorized into groups on the basis of dominant wavelength, where each group of colors is arranged to influence a vertebrate's thermoregulation in a particular manner,
    and said processor further configured to generate a control signal for controlling the dominant wavelength of light emitted from at least one light source in accordance with the selected group of colors;
    a transmitter is configured to transmit the generated control signal to said at least one light source for said at least one light source to emit light of the selected group of colors, thereby influencing the thermoregulation of the vertebrate being exposed to the light of the selected group of colors emitted by said at least one light source on the basis of said predetermined criterion;
    the transmitter configured to transmit the control signal to a climate control device configured to control a climate control system, the control signal indicating whether to lower or increase the output temperature of the climate control system depending on the selected group of colors and to influence the thermoregulation of the vertebrate,
    wherein the processor is further configured to form a basis for the categorization of color of light into groups based on properties defined by the CIE1931 chromaticity diagram.

2. The lighting control device of claim 1, further comprising a memory arranged to store said plurality of groups of color of light.

3. The lighting control device of claim 1, further comprising a user interface via which the predetermined criterion may be entered.

4. The lighting control device of claim 1, further comprising said at least one light source to be controlled.

5. The lighting control device of claim 4, further configured to be connectable to: a thermometer arranged to provide the lighting control device with a measure of ambient temperature, said measured ambient temperature determining the predetermined criterion to be used.

6. The lighting control device of claim 1, wherein the predetermined criterion is that the vertebrate is to perceive the ambient temperature as higher, for which purpose a group of colors having a dominant wavelength in the range of approximately 576-700 nm is 10 selected.

7. The lighting control device of claim 1, wherein the predetermined criterion is that the vertebrate is to perceive the ambient temperature as lower, for which purpose a group of colors having a dominant wavelength in the range of approximately 460-520 nm is selected.

8. The lighting control device of claim 1, wherein the processor is further configured to take into account color saturation when categorizing color of light into groups.

9. The lighting control device of claim 1, wherein the processor is further configured to take into account color temperature when categorizing color of light into groups.

10. The lighting control device of claim 1, wherein a reference white point of the CIE1931 chromaticity diagram is arranged to have a color temperature of about 6500 K.

11. The lighting control device of claim 1, wherein a reference white point of the CIE1931 chromaticity diagram is arranged to have a color temperature of about 3000 K.

12. The lighting control device of claim 1, wherein the output temperature of the climate control system is lowered when the predetermined criterion is to lower heating energy consumption of the climate control system, for which criterion a group of colors having a dominant wavelength in the range of about 576-700 nm is selected; or the output temperature of the climate control system is increased when the predetermined criterion is to lower coolin2018P80383WOg energy consumption in the climate control system for which criterion a group of colors having a dominant wavelength in the range of about 460-520 nm is selected.

13. A climate control system arranged to be connectable to the lighting control device of claim 1, said system further comprising the climate control device being arranged to be responsive to the control signal generated by the processor of the lighting control device, wherein characteristics of fluid discharged by the climate control device are adapted in accordance with the predetermined criterion.

14. A non-transitory computer-readable medium comprising computer program code comprising computer-executable components for causing a device to perform the steps recited in claim 1 when the computer-executable components are run on a processing unit included in the device.

* * * * *